(12) United States Patent
Yoon

(10) Patent No.: US 6,440,106 B1
(45) Date of Patent: Aug. 27, 2002

(54) BIODEGRADABLE DISPOSABLE SYRINGE

(75) Inventor: Yeo Saeng Yoon, Seoul (KR)

(73) Assignee: Boo Yoon Tech, Inc., Seoul (KR)

( * ) Notice: Subject to any disclaimer, the term of this patent is extended or adjusted under 35 U.S.C. 154(b) by 123 days.

(21) Appl. No.: 09/594,589

(22) Filed: Jun. 15, 2000

(30) Foreign Application Priority Data

Feb. 18, 2000 (KR) .............................................. 00-7741

(51) Int. Cl.[7] .............................................. A61M 5/315
(52) U.S. Cl. ..................................................... 604/218
(58) Field of Search ................................ 604/181–182, 604/187, 199, 218, 403, 523

(56) References Cited

U.S. PATENT DOCUMENTS

| 5,665,831 A | * | 9/1997 | Neuenschwander et al. ........................... 525/415 |
| 6,160,084 A | * | 12/2000 | Langer et al. ............... 528/272 |
| 6,322,797 B1 | * | 11/2001 | Mao et al. ................... 424/271 |

* cited by examiner

Primary Examiner—Sharon Kennedy
(74) Attorney, Agent, or Firm—McGuireWoods LLP

(57) ABSTRACT

The present invention relates to a biodegradable disposable syringe and more particularly, to the biodegradable disposable syringe by using a novel polyester resin composition under a specific injection molding condition, thus being able to be disposed of without causing environmental contamination.

12 Claims, 1 Drawing Sheet

BIODEGRADABLE DISPOSABLE SYRINGE

BACKGROUND OF THE INVENTION

1. Field of the Invention

The present invention relates to a biodegradable disposable syringe and more particularly, to the biodegradable disposable syringe by using a novel polyester resin composition under a specific injection molding condition, thus being able to be disposed of without causing environmental contamination.

2. Description of the Related Art

In general, biodegradable resins have been welcomed worldwide since they can be disposed of without causing environmental contamination and thus their uses are on the gradual increase these days.

There have been known various kinds of biodegradable resins, however, they have not been applicable to commercial products because either their applications were too limited or their physical properties and biodegradability were not well qualified for good molding and quality products.

The aliphatic polyester, known to have a good biodegradable property a of Macromol. SCI-Chem., A-23(3), 1986, pp. 393–409), have been used as materials in medical, agricultural, fishing and packaging industries and its fields of applications are on gradual growth. However, the conventional type of aliphatic polyesters had disadvantages that their backbone structures were too soft and heat-labile, it had low crystallinity, low melting point, difficulty in molding due to high melt index, poor tensile strength and tear strength. To make these aliphatic polyesters more applicable, many efforts have been exerted to increase the number average molecular weight of the current aliphatic polyester to have more than 30,000, however, it has not been able to obtain aliphatic polyester having a molecular weight greater than 15,000 in the conventional polycondensation system.

As a way to solve these problems conventional polyesters, a method of manufacturing aliphatic polyester resin having a number average molecular weight of greater than 30,000 by adjusting factors such as reaction temperature, degree of vacuum and amount of catalysts was disclosed in Korean Unexamined Patent Publication No 95-758; however, said aliphatic polyester resin had a low weight average molecular weight and was also heat-labile thus not considered appropriate in molding or forming.

In Korean Unexamined Patent Publication No 95-11.4171, a method of manufacturing aliphatic polyester with a high molecular weight by incorporating a monomer such as a polyhydric alcohol or a poly (at least tri-) hydric carboxylic acid is disclosed. The above process provided a way to improve the molding and forming properties of the aliphatic polyester resin by introducing the monomers into the reactor to reduce the reaction time and to diffuse the molecules within the product. However, the application of this type of polyester resin was not easy due to the decrease of physical properties such as tensile strength resulted from the drastic increase in low molecular weight polyesters. Besides, the fact that the polyester resin easily becomes a gel type makes it difficult to control the reaction for preparing the polyester resin. There is still another process for increasing the molecular weight of the aliphatic polyester resin. Unexamined Korean Patent Publication No. 95-25072, which discloses the high molecular weight aliphatic polyester resin produced by an isocyanate as a coupling material reacting to an aliphatic polyester resin having a number average molecular weight of 15,000 to 20,000 which is produced by dehydration or de-glycol reaction of the mixture of main materials of (1) an aliphatic(including cyclic type), and (2) an aliphatic (including cyclic type) dicarboxylic acid(or an anhydride thereof) with or without (3) a little of monomer of polyhydric alcohol or polyhydric carboxylic acid (or acid anhydride thereof). The aliphatic polyester resin obtained in this way had a number average molecular weight of 20,000 to 70,000. However, the above-mentioned process has a few drawbacks that it requires more reaction time thus resulting in poor productivity, and the isocyanate, a coupling material to increase the molecular weight of polyester resin, is known to be a carcinogen so necessitating an extremely careful handling of the ingredient.

On top of that there has not been found a good resolution how to deal with the waste disposal of syringes nor the syringes ever manufactured by using biodegradable polyester resins.

SUMMARY OF THE INVENTION

The conventional disposable syringes used in medical fields have been a cause of environmental contamination while its biodegradable versions have been experiencing the limited applications due to their poor physical properties. The object of the invention is therefore to provide a disposable syringe which can not only be degraded in nature without causing an environmental contamination but be applied in a broader field of medical industry by having superior physical.

DESCRIPTION OF THE INVENTION

Figure 1:
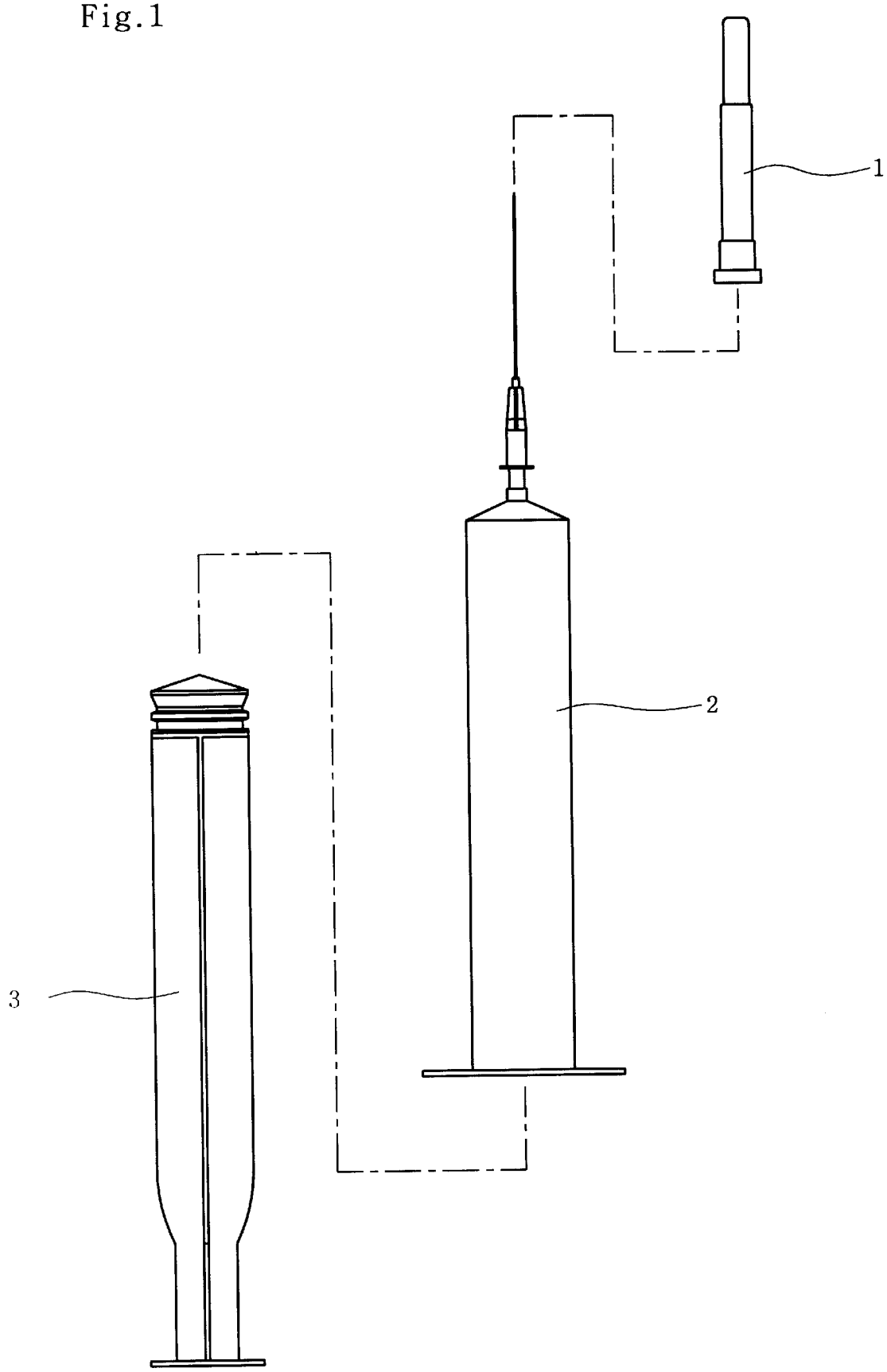
FIG. 1 shows a biodegradable disposable syringe manufactured according to the method of the present invention.

The present invention relates to a disposable syringe manufactured by means of injection molding using biodegradable polyester resin having 9,000–90,000 of number average molecular weight, 30,000–600,000 of weight average molecular weight, 40–150° C. of melting point, 0.1–50g/10 min of melt index (190° C., 2160g).

The resin composition used in the present invention comprises an aromatic dicarboxylic acid(or an acid anhydride thereof) such as dimethyl terephthalate and terephthalic acid; an aliphatic (including cyclic type) dicarboxylic acid(or an acid anhydride thereof), one or more selected from the group consisting of succinic acid and adipic acid; and an aliphatic (including cyclic type) glycol, one or more selected from the group consisting of 1,4-butanediol and ethylene glycol, by means of esterification and polycondensation reactions as disclosed in Unexamined Korean Patent Publication Nos 98-33837, 98-33834,99-56991 and 99-58816.

The polyester resin in the present invention is an aliphatic polyester resin which has superior physical properties sufficient to resolve the limitations used to be present in the conventional biodegradable types of resins by improved biodegradability ascribed to its peculiar molecular structure.

The specific physical properties of the biodegradable polyester resin in the present invention can be represented as shown in the following Table 1.

TABLE 1

| MP(° C.) | Injection (° C.) | Tensile Strength (kg/cm²) | Elongation (%) | Biodegradability (%) |
|---|---|---|---|---|
| 40–70 | 130–140 | 330 | 700 | 98 |
| 90 | 140–150 | 350 | 700 | 96 |
| 100 | 150–160 | 400 | 600 | 94 |
| 110–150 | 160–170 | 400 | 300 | 90 |

According to the present invention, the appropriate melting point of the resin ranges from 40 to 150° C., preferably from 100 to 150° C. If the melting point is below the above range the forming becomes hard to adjust properly due to low crystallinity. Products manufactured by means of injection molding as in the syringe of the present invention are used in general for producing relatively hard and durable parts, and those polyester resins with higher melting point will be more suitable for injection molding. If the temperature of injection molding is too low, the resulting syringe products will become too soft to retain its physical properties. The melting point of conventional polypropylene plastic materials falls between 180 and 220° C. and thus the properties of those materials are totally different from the one in the present invention.

Injection molding using the biodegradable resins of the present invention may be performed under general temperature conditions, however, the preferred temperature ranges from 120 to 190° C. If the molding is performed at a temperature lower than 120° C. it is hard to produce a desirable product because the resin kept within the screw will not be completely melted, while physical properties become poor due to heat decomposition if it is performed at a temperature higher than 190° C. The conventional PP resin for syringes has different injection molding temperature range, 230–275° C. However, if the resins in the present invention are molded under temperatures use for conventional resins, the resins will be inappropriate for molding because they will decomposed by heat and their physical properties will become extremely poor. Further, if the resins in the present invention are kept to stay within the screw of injection for more than 10 min the molding cannot be well proceeded or the molded product would not be able to carry the proper properties of syringe if they are molded due to heat decomposition.

For the production of highly durable syringes, the resin may be combined with a strength fortifying additive selected from the group consisting of talc, calcium carbonate, magnesium stearate, calcium sulfate, starches, sugar powder, particular anhydrous silicate and calcium phosphate, and preferably by adding 1–60 wt. % of talc or calcium carbonate based on the 100 wt. % of resin, which then enables to improve the strength of the resins in the present invention comparable to the conventional resins such as polypropylene, polystyrene or ABS resin. Calcium carbonate is inferior to talc in fortifying strength, however, it can serve as a fertilizer and prevent the soils from acidifying when it becomes biodegraded and left on the surface of soils after burial. In addition, the combustion rate of calcium carbonate added resin was better than those of resin alone or talc-added resin in the present invention.

The syringes produced in accordance with the present invention can be produced in various forms disposable syringe, pre-filled type syringe, general syringe and the like.

For example, FIG. 1 shows a biodegradable disposable syringe of the present invention having a needle cap 1, a barrel 2 and a plunger 3 manufactured by using a polyester resin composition of the present invention under a specific injection molding condition with the exception of the needle.

The following examples are intended to be illustrative of the present invention and should not be construed as limiting the scope of this invention defined by the appended claims.

PREPARATION EXAMPLE 1

To a 500 mL Erlenmeyer's flask filled with nitrogen gas 118 g of succinic acid, 121.7 g of 1,4-butanediol and 0.1 g of tetrabutyltitanate as a catalyst, were added while slowly increasing the temperature until it reached 200° C. When the temperature reached 200° C., the reaction mixture was allowed to react for 2 hrs and then theoretical mass of water was effused. Then 0.1 g of antimony acetate, 0.2 g of dibutyltin oxide, 0.07 g of tetrabutyltitanate as catalysts, and 0.2 g of trimethyl phosphate as a stabilizer were added. The temperature was raised and a polycondensation reaction was performed under 0.3 torr at 245° C. for 1.55 min. The sample of biodegradable resin taken at this point had a melt index of 15 (190° C., 2160 g), number average molecular weight of 31,000, weight average molecular weight of 190,000 and melting point of 117° C. as measured by DSC method.

PREPARATION EXAMPLE 2

To a 500 mL Erlenmeyer's flask filled with nitrogen gas, 5.9 g of succinic acid, 6.3 g of 1,4-butanediol and 0.1 g of tetrabutyltitanate as a catalyst were added to carry esterification by effusing water while slowly increasing the temperature. When the temperature reached 200° C., theoretical mass of water was effused completely to give 8.6 g of aliphatic low molecular weight polymer with its molecular weight around 10,000. Then, 76.1 g of terephthalic acid, 135.2 g of 1,4-butanediol, and 0.2 g of tetrabutyltitanate a catalyst were added to the reaction mixture to carry esterification by effusing methanol while slowly increasing the temperature. After methanol was effused completely while keeping the temperature at 205° C., 29.5 g of succinic acid and 43.8 g of adipic acid were added to carry further esterification. After water was effused while keeping the temperature at 180° C., 0.1 g of antimony trioxide, 0.3 g of dibutyltin oxide, 0.07 g of tetrabutyltitanate as catalysts, and 0.2 g of trimethyl phosphate as a stabilizer were added. The temperature was raised until it reached 245° C. and a polycondensation reaction was performed under 0.3 torr at 245° C. for 200 min. The sample of biodegradable resin taken at this point had a melt index of 2 (1.90° C., 2160 g), number average molecular weight of 61,000, weight average molecular weight of 290,000 and melting point of 117° C. as measured by DSC method.

EXAMPLE 1~2

Disposable syringes were manufactured by using polyester resins having 117° C. of melting point produced in the above Preparation Examples 1 and 2 under 1.30–1.40° C. by means of injection molding. The test results of syringes showed that 400 kg/cm² and 410 kg/cm² for tensile strength, 300% and 320% for elongation, and 90% and 92% for biodegradability rate after 45 days, respectively.

The biodegradability was measured by Organic Waste Systems[O.W.S.n.v.](Dok Noord 4, B-9000 Gent, Belgium), and tensile strength and elongation were measured by UTM.

What is claimed is:

1. A biodegradable disposable syringe manufactured by means of injection molding using biodegradable polyester resin composition having number average molecular weight of 9,000–90,000, weight average molecular weight of 30,000–600,000, melting point of 40–1.50° C., and melt index (190° C., 2160 g) of 0.1–50 g/10 min.

2. The biodegradable disposable syringe according to claim 1, wherein said polyester resin composition is an aliphatic polyester resin comprising:

1) an aromatic dicarboxylic acid which contains an aromatic group;
2) succinic acid or adipic acid;
3) 1,4-butanediol or ethylene glycol; and manufactured by esterification and polycondensation.

3. The biodegradable disposable syringe in accordance to claim 1, wherein talc or calcium carbonate is added as a strength fortifier in the ratio of 1–60% by weight to said polyester resin composition.

4. The biodegradable disposable syringe in accordance to claim 1, wherein said injection molding is performed at 150–220° C.

5. The biodegradable disposable syringe in accordance to claim 1, wherein melting temperature of said polyester resin is 100–150° C.

6. The biodegradable disposable syringe in accordance to claim 1, wherein the types of said syringes include a general disposable syringe, a pre-filled type syringe and a general syringe.

7. The biodegradable disposable syringe of claim 2, wherein the aromatic dicarboxylic acid or the acid anhydride thereof is dimethyl phthalate or terephthalic acid.

8. The biodegradable disposable syringe according to claim 1, wherein said polyester resin composition is an aliphatic polyester resin comprising:

1) an aromatic dicarboxylic acid or an acid anhydride thereof which contains an aromatic group;
2) an aliphatic dicarboxylic acid or an acid anhydride thereof;
3) an aliphatic glycol; and manufactured by esterification and polycondensation.

9. The biodegradable disposable syringe of claim 8, wherein the aromatic dicarboxylic acid or the acid anhydride thereof is dimethyl phthalate or terephthalic acid.

10. The biodegradable disposable syringe of claim 8, including a cyclic-type aliphatic dicarboxylic acid.

11. The biodegradable disposable syringe of claim 8, including a cyclic-type aliphatic glycol.

12. A disposable syringe by the polycondensation of dicarboxylic acid and a glycol, the syringe comprising:

a biodegradable polyester resin composition prepared by polycondensation after esterification of (i) an aromatic dicarboxylic acid or an anhydride thereof selected from the group consisting of dimethyl terephthalate and terephthalic acid, and (ii) succinic acid or a mixture of succinic acid and adipic acid with (iii) succinic acid or a mixture of succinic acid and adipic acid with an aliphatic glycol selected from the group consisting of 1,4-butanediol and ethylene glycol, wherein said polyester resin has a number average molecular weight of 9,000–90,000, a weight average molecular weight of 30,000–600,000, a melting point of 100–150° C., and a melt index (190° C., 2160 g) of 0.1–50 g/10 min, and wherein said syringe is produced by injection molding at above 150–190° C.

* * * * *